United States Patent [19]

Courtois et al.

[11] Patent Number: 5,569,593
[45] Date of Patent: Oct. 29, 1996

[54] PILOCARPIN PRODUCTION PROCESS

[75] Inventors: Didier Courtois, Orleans; Vincent Petiard, Tours; André Touche, Monts, all of France

[73] Assignee: Nestec S.A., Vevey, Switzerland

[21] Appl. No.: 404,408

[22] Filed: Mar. 14, 1995

[30] Foreign Application Priority Data

Mar. 21, 1994 [EP] European Pat. Off. ............... 94104402

[51] Int. Cl.$^6$ .............................. C12P 17/16; C12N 5/04; A01H 4/00

[52] U.S. Cl. ...................... 435/118; 435/119; 435/240.48; 435/240.5

[58] Field of Search ................................. 435/118, 121, 435/119, 240.48, 240.5

[56] References Cited

U.S. PATENT DOCUMENTS 5,059,531  10/1991  Reuther .................................... 435/118
5,107,066  4/1992  Ashikawa et al. .................. 435/240.4

FOREIGN PATENT DOCUMENTS 0283051   9/1988  European Pat. Off. .
WO90/12102  10/1990  WIPO .

Primary Examiner—Herbert J. Lilling
Attorney, Agent, or Firm—Pennie & Edmonds

[57] ABSTRACT

The present invention concerns a process for the production of pilocarpine, in which root formation is induced from part of a plant of the genus Pilocarpus, the said roots are cultivated in vitro in a culture medium and pilocarpine is isolated from the roots and/or the medium.

19 Claims, No Drawings

PILOCARPIN PRODUCTION PROCESS

TECHNICAL FIELD

The present invention concerns a process for the production of pilocarpine.

BACKGROUND ART

Pilocarpine in is an alkaloid having miotic and parasympathomimetic properties which is the basis of various pharmaceutical preparations and particularly ophthalmological preparations. Used as a miotic substance, it, for example, reduces the intraocular pressure in the eye. Pilocarpine is thus employed preferably in the treatment of glaucoma.

Production of pilocarpine is at the present time principally carried out by its extraction from the leaves of wild Pilocarpus. In point of fact, the production of pilocarpine by chemical or biochemical methods remains difficult and arduous. However, cultivation of Pilocarpus is long, difficult and at the present time not well developed. Indeed, Pilocarpus seeds only retain their power of germination for a very short time and plantlets grow particularly slowly.

U.S. Pat. No. 5059531 describes a process for the vegetative propagation of Pilocarpus plants. In this process, a suspension of undifferentiated Pilocarpus cells is subjected to hormone treatment which induces differentiation in vitro of cells into buds (or leaves). These buds are then subjected to hormone treatment which induces the formation of roots. Plantlets are thus obtained which will subsequently be cultivated in fields with the aim of harvesting the leaves. This process thus enables a large number of identical Pilocarpus plantlets to be obtained rapidly, but it does not resolve the disadvantages associated with their cultivation in the field.

U.S. Pat. No. 5,059,531 also describes the possibility of extracting pilocarpine directly from induced buds. However, this in vitro cultivation of buds has disadvantages. First of all, buds do not have the capacity to multiply as undifferentiated cells do, the biomass of the culture thus increasing solely due to the lengthening of buds. Cultivation is thus long and limited in volume. Secondly, the concentration of pilocarpine, in buds is less than that present in the plant by a factor of 10 and the quantity of pilocarpine that can be purified is thus also limited.

SUMMARY OF THE INVENTION

The present invention aims at overcoming the disadvantages of the prior art and thus proposes a process enabling easy production of pilocarpine to be achieved.

For this purpose, root formation is induced from part of a plant of the genus Pilocarpus, the roots are cultivated in vitro in a culture medium and pilocarpine is isolated from the roots and/or the medium.

In a first method of carrying out the invention, root formation is induced from an organ or undifferentiated cells of Pilocarpus in an induction medium comprising at least one auxine and one cytokinine, the roots are cultivated in vitro in a culture medium and pilocarpine is then isolated from the roots and/or the medium.

Similarly, in a second method of carrying out the invention, root formation is induced from a Pilocarpus organ using *Agrobacterium rhizogenes* and the roots are cultivated in vitro in a culture medium and pilocarpine is then isolated from the roots and/or the medium.

DETAILED DESCRIPTION OF THE PREFERRED EMBODIMENTS

In the rest of the description, the expression "a part of a plant" is used to mean undifferentiated cells or an organ of Pilocarpus.

The expression "undifferentiated cells" is also used in the sense of cells which have an ability under certain conditions to multiply in the form of a callus or a cell suspension, and then under certain conditions to differentiate into one or more cellular types which can become organized into a plant organ, such as a bud or a root, for example.

Similarly, the term "callus" is understood to mean a macroscopic mass of undifferentiated plant cells in a culture on a solid nutrient medium.

Finally, the expression "cell suspension" is understood to mean undifferentiated cells which can form microscopic masses when cultured in a liquid nutrient medium.

In vitro culture of Pilocarpus roots with a view to isolating pilocarpine has real advantages compared with traditional methods. In point of fact, since Pilocarpus roots have the natural capacity of increasing in length and multiplying, the cultivation of Pilocarpus root is not limited in volume and moreover is more rapid than that of buds. In addition, since the concentration of pilocarpine in the roots is equivalent to that present in the leaves of the original plant, roots thus constitute an important source of pilocarpine. Finally, the culture medium contains a not inconsiderable quantity of pilocarpine liberated by the roots and this pilocarpine can thus also be purified.

In order to put the first method of carrying out the invention into operation, root formation is thus induced from an organ or undifferentiated cells of Pilocarpus in an induction medium comprising at least one auxine and one cytokinine.

All species of Pilocarpus can serve as a source of organs or cells for root culture according to the present invention. Use can thus be made of the species *Pilocarpus pennatifolius, Pilocarpus heterophyllus, Pilocarpus microphyllus* and *Pilocarpus jaborandi*, for example.

In the first preferred method of carrying out the invention, a root culture can be induced from a Pilocarpus organ with the aid of plant hormones. This organ can be a fragment of leaf, root, stem or parts of flowers from plantlets or fully grown trees. For this, the organ having a length of 0.5 to 10 cm can be sterilised by known means, the organ is then put into a solid induction medium containing rhizogenesis-inducing hormones at a temperature of 18° C. to 34° C., preferably 24° C. and the organ is cultivated for several weeks according to a standard procedure in the light or in the dark, preferably in the dark. A proliferation of roots can thus be obtained from one or more calluses which are formed on the organ from the first weeks of culture. The said roots then have root structures identical to those of the roots of a plant.

The induction medium comprising hormones can be a medium with a base usually employed in the in vitro culture of plant cells. Preferably, a MURASHIGE and SKOOG medium is used, with an addition of SKOOG or LINSMAYER vitamins (Physiol. Plant., 1962, vol. 15, p. 473; Physiol. Plant., 1965, vol. 18, p. 100). The concentration of the components of the medium can be varied within a certain range without, in spite of this, affecting the process according to the present invention and in particular the concentration of glucides (saccharose, glucose) can be varied from 1 to 120 g/l, preferably from 10 to 60 g/l. The concentration of macro-elements can also be reduced by a factor of 2.

Finally, the pH value of the medium can vary from 4 to 8, and preferably a pH of about 5.6 is used which is the pH of the medium before sterilization.

Preferably, an auxine is used in the induction medium at a concentration of 0.1 to 10 mg/l, for example 1 mg/l, and a cytokinine at a concentration of 0.01 to 2 mg/l, for example 0.1 mg/l. In addition, the auxine can be selected from the following molecules: α-naphthalene acetic acid (NAA), β-indol butyric acid (IBA), 2,4-dichlorophenoxyacetic acid (2.4-D), β-indol acetic acid (IAA), for example. In addition, the cytokinine can be selected from the following molecules: kinetine (KIN), benzylaminopurine (BAP), and isopentenyladenosine (IPA), for example.

The presence of at least one auxine and one cytokinine in the induction medium thus brings about the formation of a callus at the end of a few weeks, generally 2 to 5, and root proliferation at the end of six weeks. The callus can also be cultivated on its own. For this purpose, the callus obtained in the first 5 weeks of induction in a culture, is put on a semi-solid nutrient medium usually employed for cultivating plant cells in vitro. A callus can then be preserved for years by successive planting out on a fresh medium. The callus can also be planted out in a stirred traditional liquid culture medium. A suspension of undifferentiated cells is thus obtained.

In the first method of carrying out the invention, root formation can also be induced from undifferentiated Pilocarpus cells using plant hormones. These undifferentiated cells which can be a callus or a cell suspension, can be subjected to inductive rhizogenesis treatment such as described above. For this purpose, the same MURASHIGE and SKOOG medium can be used and the same hormone balance described for the preceding induction medium. Preferably, a semi-solid induction medium is used for a callus, and a liquid induction medium for a cell suspension. A proliferation of roots is thus obtained from the callus or undifferentiated cells in suspension.

Roots obtained according to the first method of carrying out the invention can then be cultivated in vitro on a traditional culture medium, for example a semi-solid or liquid MURASHIGE and SKOOG medium, preferably a stirred liquid one. If roots have been obtained from a callus or an organ, only the roots can then be cultivated, that is to say roots separated from the callus or from the organ, or roots can be directly cultivated with the callus or organ. In particular, the hormone balance of the culture medium can be different from that used for the rhizogenesis inducing medium. At least one auxine can then be used at a concentration of 0.1 to 10 mg/l, or a combination can be used of at least one auxine at a concentration of 0.1 to 10 mg/l and one cytokinine at a concentration of 0.01 to 2 mg/l. A root culture is thus obtained in which the biomass increases by multiplication and extension of the said roots.

In a second preferred method of carrying out the invention, root formation is induced from a Pilocarpus organ using *Agrobacterium rhyzogenes*. In particular, to induce root formation, the organ can be incubated in a suspension of *Agrobacterium rhyzogenes* for 30 minutes to 24 hours, and the induced organ can then be cultivated in a nutrient medium until roots develop.

The bacterial suspension can thus be a traditional culture of *Agrobacterium rhyzogenes* aged for at least 20 hours, for example. In addition, after incubation the bacteria can be killed with the aid of an antibiotic.

In particular, the Pilocarpus organ can be a juvenile organ, that is to say a plant organ which is being formed or has just been formed, such as a bud, a young leaf, a young root or an embryo. Preferably, an apical bud is used as the juvenile organ or a zygotic embryo, or a differentiated organ from a callus, for example a bud or a somatic embryo differentiated due to a tradition treatment using plant hormones.

The nutrient medium can in addition be a medium with a base usually employed in the in vitro culture of plant cells. Preferably, a semi-solid MURASHIGE and SKOOG medium is used with the addition of SKOOG or LINSMAYER vitamins.

Certain cells of the induced organ are transformed by *Agrobacterium rhizogenes* and are thus capable of producing auxines naturally. Consequently, the organ can be cultivated in a nutrient medium not containing plant hormones, without in spite of this reducing the number of root points which form to a noticeable extent. One can however prefer to add at least one auxine to the nutrient medium in order to encourage the survival of the organ until roots develop. An auxine concentration can thus be used such as is normally employed for in vitro cultivation of an organ, for example. Similarly, at least one auxine and one cytokinine can be added to the nutrient medium in concentrations such that they induce supplementary root development, for example.

Transformed roots of Pilocarpus then proceed to develop from the induced organ at the end of about 4 to 10 weeks. Roots are then obtained of the "hairy root" type, which can be planted out into a culture medium not containing plant hormones. This culture medium can thus be a medium with a base usually employed for the in vitro culture of plant cells. Preferably, a MURASHIGE and SKOOG liquid medium is used with the addition of SKOOG or LINSMAYER vitamins, for example. Finally, at least one auxine can be added to the culture medium in order to encourage roots to grow in the culture medium, or at least one auxine and at least one cytokinine can be added to the nutrient medium in concentrations such that they induce supplementary root development, for example.

Finally, in the process according to the present invention pilocarpine can be extracted from a culture of the roots of Pilocarpus using roots and/or the culture medium. This culture can have been obtained from one of the two methods of inducing rhizogenesis described above. Preferably, roots and/or the culture medium are concentrated, dried or lyophilised before extracting pilocarpine from them.

A traditional method of purification can be used for the extraction. A quantity of pilocarpine can thus be obtained per dry biomass equivalent to that found in the leaves of the original plant. For example, for *Pilocarpus pennatifolius* 300 to 500 μg/g of dry biomass are obtained, that is 300 to 500 mg of pilocarpine per kilogram of biomass.

Pilocarpine prepared according to the present invention is identical to that isolated from the leaves by a traditional method. It can thus be used in pharmaceutical specialities applied in particular to the treatment of glaucoma.

Pilocarpine can be purified and analysed in greater detail with the aid of the methods described below. Percentages are given by volume.

Purification methods

Pilocarpine biosynthesized from a root culture is extracted in the following manner.

The roots (or rhizogenic calluses) and/or the culture medium are dried or concentrated by a traditional method. The roots and/or the culture medium are crushed and the whole is extracted with stirring or by percolation with a water-alcohol mixture, preferably 95° ethyl alcohol with the addition of an acid at concentrations of 1 to 10%.

Hydrochloric acid is preferably used in a proportion of 99 of alcohol: 1 of acid.

The solid is filtered off and then rinsed with the same solvent. A volume of water, preferably 30% (based on the alcohol volume) is added to the filtrate. The alcohol is evaporated off under vacuum (80 mbar and at 50° C.). The concentrated aqueous phase is once more filtered to remove water insoluble matter.

The filtrate is then made alkaline to pH values of between 5.5 and 9.5 with alkaline agents which can be strong bases with or without dilution or salts of weak acids and strong bases. The alkaloids are then extracted with the aid of a water-immiscible solvent, preferably a chlorinated solvent, in particular chloroform or methylene chloride. The alkaline aqueous phase is extracted until all the alkaloids have been removed, for example in three successive extractions.

The organic phases are combined and dried over a dehydrating agent, preferably sodium sulphate. The alkaloid extract is obtained by evaporation of the organic solvent, the main alkaloid being pilocarpine which can be crystallized in the form of the salts of inorganic or organic acids.

Qualitative analysis

The alkaloid extract is analysed qualitatively by thin layer chromatography on silica gel (Merck 60F254, Ref. 5715) by mono- or bi-dimensional elution with the following eluents:

Eluent 1: $CHCl_3$ (90%)-MeOH (10%).

Eluent 2: ethyl acetate (50%), methyl ethyl ketone (30%), formic acid (10%), water (10%).

The alkaloids are revealed with DRAGENDORFF reagent.

Quantitative analysis

The alkaloid extract containing purified pilocarpine is analysed quantitatively by high performance liquid chromatography with a NOVAPAK C18 column (Ref 86344, WATERS) in the following manner:

Elution under isocratic conditions. Phosphate/acetonitrile buffer mixture with proportions of 1 to 5 of organic solvent.

The different compounds are detected by UV absorption at 220 nm or by refractometry. Analyses are carried out with external pilocarpine nitrate standards.

The alkaloid extract containing purified pilocarpine can also be analysed quantitatively by gas chromatography with a CPSil 5CB CHROMPACK (Ref 7740) capillary column. A temperature programme from 150° to 220° C. is used for this with a FID detector. Analyses are carried out using an external pilocarpine nitrate standard or using an internal lupanine perchlorate standard.

EXAMPLES

The following examples are given as an illustration of the present process for producing pilocarpine.

Example 1

Roots are obtained from fragments of leaves from *Pilocarpus pennatifolius* Lem cultivated in a greenhouse.

Leaves are gathered from *Pilocarpus pennatifolius* Lem plants. After disinfection, the plant material is cut up into 1 $cm^2$ fragments and placed on a semi-solid MURASHIGE and SKOOG agar-agar nutrient medium (to which SKOOG vitamins have been added) containing 1 mg/l of NAA and 0.1 mg/l of KIN. Cultures are made in sterile Petri dishes (diameter: 55 mm or 100 mm), in darkness and at 24° C. After 4 to 6 weeks culture, the first roots appear from the callus which is formed on the cultivated organ. After at least 6 weeks the roots obtained are separated from the leaf fragments or calluses and then transferred to the preceding semi-solid MURASHIGE and SKOOG medium and regularly planted out on the same medium.

Example 2

The plant material described in Example 1 is placed on the semi-solid MURASHIGE and SKOOG nutrient medium (to which LINSMAYER vitamins have been added and in which the concentration of macro-elements is divided by two) containing 1 mg/l of NAA and 0.1 mg/l of BAP. After 6 weeks the roots and the callus are transferred directly to the preceding medium and planted out regularly on this same medium.

Example 3

Calluses of *Pilocarpus heterophyllus* are used, planted out for 6 years in a standard culture medium.

These calluses are planted out on a MURASHIGE and SKOOG medium with a base comprising 10 mg/l of NAA and 1 mg/l of KIN. These calluses are then transferred to the same base medium in the presence of 1 mg/l of NAA and 0.06 mg/l of KIN. Root development is obtained at the end of a few weeks.

Example 4

The roots obtained in example 1 are planted out on the MURASHIGE and SKOOG liquid medium (without agar-agar) with the addition of LINSMAYER vitamins and comprising 1 mg/l of NAA and 0.1 mg/ 1 of BAP.

For this, the roots are replanted every 6 weeks for a duplication time of three weeks and an inoculation rate of 20 g of fresh biomass per litre of medium. The roots are cultivated in 250 ml Erlenmeyer flasks (100 ml of medium) at 24° C., in darkness and with stirring at 100 rpm. The roots develop by elongation and ramification.

The roots of example 2 (which are not separated from their original explant) are also planted out and then cultivated in the same manner as above.

Two root cultures are thus obtained having essentially the same growth characteristics.

Example 5

The calluses of *Pilocarpus heterophyllus* such as described in example 3 are transferred to the MURASHIGE and SKOOG base base medium with the addition of 2,4-D (0.5 mg/l) and KIN (0.03 mg/l). After 6 weeks, somatic embryos and buds develop from calluses which have become organogenic. These calluses are then incubated for 3 hours in a bacterial suspension of *Agrobacterium rhizogenes* aged for 24 hours. The bacterial strain used is a virulent A4 strain containing the wild Ri plasmid and the binary p35S-GUS-INT plasmid (G. Vancanneyt et al., Mol. Gen. Genet., 1990, 245–250) and cultivated on a MYA medium (M. TEPFER et al., Microbiol. Sci., 1987, 24–28).

The p35S-GUS-INT binary plasmid comprises the GUS reporter gene and the NPTII selection gene. The presence of the PIV2 intron in the phase coding for the GUS gene avoids any possible expression of the GUS gene due to residual bacteria.

After incubation, the organogenic calluses are transferred to the MURASHIGE and SKOOG nutrient medium with the addition of 2,4-D (0.5 mg/l) and KIN (0.03 mg/l). At the end of 2 weeks, samples of plant material are subjected to a histochemical β-glucoronidase activity test according to he R. A. Jefferson protocol (Plant Molecular Biology Reporter, Vol. 5, no. 4, 1987, 387–405). The blue coloration observed characterizes expression of the GUS gene. Traditional analyses by PCR and Southern blot (J. Spiral et al., in ASIC, 15th colloquium, Montpellier, 1993), show in addition its integration into the plant cell genome.

At the end of 4 weeks, roots develop from organs differentiated from the callus. These organs and these roots are then transferred to the liquid MURASHIGE and SKOOG culture medium not containing plant hormones. Continuous development of transformed roots is then observed.

Example 6

Organogenic calluses incubated in a suspension of *Agrobacterium rhizogenes* such as described in example 5, are transferred to the MURASHIGE and SKOOG nutrient medium with the addition of 0.5 mg/l of 2,4-D. At the end of about 5 weeks, roots develop from the organs. Only the roots are then transferred to a MURASHIGE and SKOOG liquid culture medium comprising 1 mg/l of NAA. Continuous development of transformed roots is then observed.

Example 7

Organogenic calluses incubated in a suspension of *Agrobacterium rhizogenes* such as described in example 5, are transferred to a MURASHIGE and SKOOG nutrition medium not containing plant hormones. At the end of about 5 weeks, roots develop from the organs. Only the roots are then transferred to a MURASHIGE and SKOOG liquid culture medium comprising 1 mg/l of NAA and 0.1 mg/l of KIN. Continuous development of transformed roots is then observed.

Example 8

The root culture such as described in example 1 is placed in a 10 litre bio-reactor (NBS, France) fitted with a blade stirrer, at an inoculation density of 20 g per litre. The conditions for root culture and growth are identical to those observed in Erlenmeyer flasks (stirring: 100 rpm, aeration: 0.5 v/v/min).

Example 9

Pilocarpine can be extracted from root cultures such as described in examples 1 to 8 by the purification method described above. The quantities of pilocarpine obtained from these cultures, determined by the quantitative method described above, are of the order of 300 to 500 μg/g of dry matter. These quantities are equivalent to those found in the leaves of the original plant.

We claim:

1. A process for the production of pilocarpine, which comprises inducing root formation from a part of a plant of the genus Pilocarpus; cultivating only the roots in vitro in a culture medium, and isolating pilocarpine from the cultivated roots or culture medium.

2. The process according to claim 1, in which root formation is induced from an organ or undifferentiated cells of the plant in an induction medium comprising at least one auxine and one cytokinine.

3. The process according to claim 2, wherein the auxine is present in the induction medium at a concentration of 0.1 to 10 mg/l and the cytokinine is present at a concentration of 0.01 to 2 mg/l.

4. The process according to claim 2, wherein the organ is a fragment of leaf, root, or stem or parts of flowers from plantlets or adult trees, or that the undifferentiated cells are a callus or a cell suspension.

5. The process according to claim 1, wherein the culture medium comprises at least one auxine, or the combination of an auxine and a cytokinine.

6. The process according to claim 5, wherein the culture medium comprises at least one auxine at a concentration of 0.1 to 10 mg/l or at least one auxine at a concentration of 0.1 to 10 mg/l in combination with at least one cytokinine at a concentration of 0.01 to 2 mg/l.

7. A process for the production of pilocarpine, which comprises inducing root formation from a part of a plant of the genus Pilocarpus, in which root formation is indued with the aid of in vitro *Agrobacterium rhizogenes*; cultivating only the roots in vitro in a culture medium, and isolating pilocarpine from the cultivated roots or culture medium.

8. The process according to claim 7, wherein root formation is induced by incubating the plant part in a suspension of the *Agrobacterium rhizogenes* for at least about 30 minutes followed by cultivating the induced organ in a nutrient medium until roots develop.

9. The process according to claim 8, wherein the nutrient medium comprises at least one auxine, one cytokinine, or the combination of an auxine and a cytokinine.

10. The process according to claim 9, wherein the plant part is a juvenile organ.

11. The process according to claim 10, wherein the juvenile organ is an apical bud, a somatic embryo or an organ differentiated from a callus.

12. The process according to claim 8, wherein the nutrient medium is MURASHIGE and SKOOG, optionally containing SKOOG or LINSMAYER vitamins.

13. The process according to claim 2, wherein the induction medium is MURASHIGE and SKOOG, optionally containing SKOOG or LINSMAYER vitamins.

14. The process according to claim 1, wherein the culture medium is MURASHIGE and SKOOG, optionally containing SKOOG or LINSMAYER vitamins.

15. The process according to claim 1, wherein roots are cultivated in a liquid culture medium.

16. The process according to claim 1, wherein the roots of Pilocarpus are roots of *Pilocarpus pennatifolius, Pilocarpus heterophyllus, Pilocarpus microphyllus*, or *pilocarpus jaborandi*.

17. A process for the production of pilocarpine, which comprises inducing root formation from undifferentiated cells or an organ of a plant of the genus Pilocarpus which includes thereon one or more callus tissues; cultivating the roots in vitro in a culture medium, and isolating pilocarpine from the cultivated roots or culture medium.

18. The process according to claim 17, wherein the culture m m comprises at least one auxine, or the combination of an auxine and a cytokinine.

19. The process according to claim 17, in which root formation is induced with the aid of in vitro *Agrobacterium rhizogenes*.

\* \* \* \* \*